United States Patent
Yoshida et al.

(10) Patent No.: US 9,623,443 B2
(45) Date of Patent: Apr. 18, 2017

(54) ULTRASONIC DEVICE UNIT, PROBE, ELECTRONIC DEVICE AND ULTRASONIC IMAGING DEVICE

(71) Applicant: SEIKO EPSON CORPORATION, Tokyo (JP)

(72) Inventors: Kazuki Yoshida, Fujimi-machi (JP); Kazuyuki Kano, Aichi (JP); Yusuke Nakazawa, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 150 days.

(21) Appl. No.: 14/641,759

(22) Filed: Mar. 9, 2015

(65) Prior Publication Data
US 2015/0266058 A1    Sep. 24, 2015

(30) Foreign Application Priority Data
Mar. 20, 2014    (JP) .................................. 2014-058546

(51) Int. Cl.
*B06B 1/06*    (2006.01)
*A61B 8/00*    (2006.01)

(52) U.S. Cl.
CPC .......... *B06B 1/0622* (2013.01); *A61B 8/4427* (2013.01); *A61B 8/4483* (2013.01)

(58) Field of Classification Search
CPC .... B06B 1/0622; A61B 8/4483; A61B 8/4427
See application file for complete search history.

(56) References Cited

U.S. PATENT DOCUMENTS

| | | |
|---|---|---|
| 2013/0226005 A1 | 8/2013 | Kano |
| 2013/0338502 A1* | 12/2013 | Onishi ................. A61B 8/4494 600/443 |
| 2014/0103781 A1 | 4/2014 | Nakamura et al. |
| 2014/0241112 A1 | 8/2014 | Kano |

FOREIGN PATENT DOCUMENTS

| | | |
|---|---|---|
| JP | 2008-079909 A | 4/2008 |
| JP | 4776344 B2 | 9/2011 |
| JP | 2011-255024 A | 12/2011 |
| JP | 2013-172799 A | 9/2013 |
| JP | 2014-078906 A | 5/2014 |
| JP | 2014-161707 A | 9/2014 |

\* cited by examiner

*Primary Examiner* — Peter Luong
(74) *Attorney, Agent, or Firm* — Global IP Counselors, LLP

(57) ABSTRACT

An ultrasonic device unit includes a substrate having a planar part and a recess part recessed from the planar part, an ultrasonic device which has an element array including a plurality of thin film ultrasonic transducer elements disposed in an array and is disposed in the recess part, a first flexible printed board, one end of which is superimposed on a portion of an array surface of the ultrasonic device and connected to the same, the other end of which is superimposed on a portion of the planar part and connected to the same, wherein the array surface of the ultrasonic device which the one end of the first flexible printed board is superimposed on is positioned within a plane including the planar part or a plane outside of the recess part.

13 Claims, 8 Drawing Sheets

ULTRASONIC DEVICE UNIT, PROBE, ELECTRONIC DEVICE AND ULTRASONIC IMAGING DEVICE

BACKGROUND

1. Technical Field

The present invention relates to an ultrasonic device unit, as well as a probe, an electronic device and an ultrasonic imaging device, which utilize the same.

2. Related Art

An ultrasonic device unit having an ultrasonic device with bulk type piezoelectric elements being disposed in an array is generally known. For example, in an ultrasonic device unit described in JP-A-2008-79909, a recess part is formed to be recessed from a plane, and the ultrasonic device is disposed in the recess part. The ultrasonic device has bulk type piezoelectric elements which are vertically interposed between a common electrode and a signal electrode. The common electrode is connected to a land on the plane by means of wire bonding, wherein a flexible substrate is connected to the signal electrode at a lower position than the plane.

JP-A-2008-79909 is an example of related art.

In the configuration described in JP-A-2008-79909, the flexible substrate is connected to the signal electrode at a lower position than the plane, and bent between a wall surface of the recess part and the ultrasonic device. But as the distance (length) of the flexible substrate is shortened relative to its width, it becomes more difficult to bend the flexible substrate. If no sufficient distance is provided between the wall surface of the recess part and the ultrasonic device, it is difficult to make a connection using a flexible substrate. Therefore, a predetermined distance is required between the wall surface of the recess part and the ultrasonic device, thereby making it difficult to miniaturize the ultrasonic device.

In view of the above problem, a structure contributing to secure miniaturization is desired for the ultrasonic device unit.

SUMMARY (1) An aspect of the invention refers to an ultrasonic device unit comprises a substrate having a planar part and a recess part recessed from the planar part; an ultrasonic device which has an element array including a plurality of thin film ultrasonic transducer elements disposed in an array and is disposed in the recess part; a first flexible printed board, one end of which is superimposed on a portion of an array surface of the ultrasonic device and connected to the same, the other end of which is superimposed on a portion of the planar part and connected to the same, wherein the array surface of the ultrasonic device which the one end of the first flexible printed board is superimposed on is positioned within a plane including the planar part or a plane outside of the recess part.

The ultrasonic device is received in the recess part. The ultrasonic device is disposed in the portion of the substrate that is recessed from the plane. The flexible printed board is superimposed on the ultrasonic device disposed in the recessed portion and connected to the same. Accordingly, compared to a case that the ultrasonic device is disposed at the planar part of the substrate, it is possible to suppress a bending of the flexible printed board. As the distance (length) of the flexible printed board decreases relative to its width, the flexible printed board is prevented from bending. And as the flexible printed board is kept from the bending, it is possible to shorten the length of the flexible printed board for connection of the flexible printed board. Accordingly, it is possible to securely miniaturize the ultrasonic device unit.

Herein, the wording "is positioned within a plane outside of the recess part" does not indicate an inside of the recess part of the planar part of the substrate but refers to an inside of a plane positioned outside on an opposite side. For example, in case the depth of the recess part is less than the thickness of the ultrasonic device, the array surface of the ultrasonic device which the one end of the flexible printed board is superimposed on is positioned opposite to the bottom surface side of the recess part. In addition, it is not particularly limited to the configuration that the array surface strictly coincides with the plane, and the position of the plane can be varied within the range exhibiting the above advantageous effect. The ultrasonic device is provided with the ultrasonic transducer elements disposed in an array, in which an element surface acting as an output surface of ultrasonic waves of the ultrasonic transducer element is disposed so as to be positioned at a predetermined plane, namely the array surface.

(2) It is possible to dispose a terminal connected to a terminal on the first flexible printed board in the planar part of the substrate, wherein the recess part has two mutually intersecting perpendicular surfaces at its lateral surfaces, and wherein the ultrasonic device abuts against the lateral surfaces. In the substrate, the lateral surface of the recess part can be positioned precisely in relation to the terminal on the planar part. Accordingly, when the ultrasonic device received in the recess part abuts against the two lateral surfaces, it is possible to precisely position the ultrasonic device in relation to the terminal on the plane. With this configuration, it is possible to realize a secure connection of the flexible printed board with the substrate and the ultrasonic device.

(3) The array surface of the ultrasonic device which the one end of the first flexible printed board is superimposed on can be positioned within a plane including the planar part. The first flexible printed board is prevented from bending. It is possible to minimize the length of the first flexible printed board for connection of the first flexible printed board. With this configuration, it is possible to securely miniaturize the ultrasonic device unit. Besides, in such an ultrasonic device unit, the first flexible printed board can be positioned only on the basis of in-plane displacement, making it possible to connect the first flexible printed board to the ultrasonic device and the substrate after the ultrasonic device is fixed to the substrate.

(4) The ultrasonic device unit can be further provided with a second flexible printed board, one end of which is superimposed on a portion of the array surface of the ultrasonic device and connected to the same, the other end of which is superimposed on a portion of the planar part and connected to the same, wherein a first direction is directed towards the other end from the one end of the first flexible printed board, and wherein a second direction is opposite to the first direction and directed towards the other end from the one end of the second flexible printed board. For use of the ultrasonic device unit, the ultrasonic device is generally pressed to an object to be detected. When the ultrasonic device is displaced in the first direction along the surface of the object to be detected, for example, a shearing force acts on the ultrasonic device in the second direction. Then, the first flexible printed board is subjected to a tensile force. The first flexible printed board prevents the ultrasonic device from being displaced while resisting to the tensile force. In contrast, when the ultrasonic device is displaced in the second direction along the surface of the object to be detected, a shearing force acts on the ultrasonic device in the first direction. Then, the second flexible printed board is subjected to a tensile force. The second flexible printed board prevents the ultrasonic device from being displaced while resisting to the tensile force. With this configuration, it is possible to prevent the ultrasonic device from being displaced in relation to the substrate.

(5) The array surface of the ultrasonic device which the one end of the first flexible printed board and the one end of the second flexible printed board are superimposed on can be positioned within a plane including the planar part. The first flexible printed board and the second flexible printed board can be prevented from bending. For connection of the first flexible printed board and the second flexible printed board, it is possible to minimize the length of each flexible printed board. With this configuration, it is possible to securely miniaturize the ultrasonic device unit. Besides, in such an ultrasonic device unit, each flexible printed board can be connected to the ultrasonic device and the substrate after the ultrasonic device is fixed to the substrate.

(6) The ultrasonic device can include a device substrate which defines opening parts individually for the thin film ultrasonic transducer elements and is provided at a first surface thereof with a vibration film closing the opening parts; and a plate member which is attached to a second surface of the device substrate opposite to the first surface of the device substrate, wherein the plate member defines a ventilation path which is connected to interior spaces of the opening parts and opens at a surface facing a bottom surface of the recess part, and wherein a through-hole is formed in the bottom surface of the recess part so as to run through the substrate. The device substrate is reinforced with the plate member, thereby making it possible to assure the rigidity of the device substrate even when the opening parts are formed in an array. The ultrasonic device can be prevented from being damaged for being handled, and thereby easily handled. In this configuration, interior spaces of the opening parts communicate with an exterior space of the substrate through the ventilation path and the through-hole. Ventilation is assured between the interior spaces of the opening parts and the exterior space of the substrate. Therefore, the interior spaces of the opening parts are not hermetically closed. The interior spaces of the opening parts easily follow a fluctuation in surrounding pressure. With this configuration, the thin film ultrasonic transducer elements can be securely prevented from being damaged. If the interior spaces of the opening parts are hermetically closed, the thin film ultrasonic transducer elements may be damaged due to the fluctuation in the surrounding pressure.

(7) The ultrasonic device can include a device substrate which defines opening parts individually for the thin film ultrasonic transducer elements and is provided at a first surface thereof with a vibration film closing the opening parts; and a plate member which is attached to a second surface of the device substrate opposite to the first surface of the device substrate, wherein the plate member defines a ventilation path which is connected to interior spaces of the opening parts and opens at a surface facing a bottom surface of the recess part, and wherein a void space can be formed between the lateral surface of the recess part and the ultrasonic device. The device substrate is reinforced with the plate member, thereby making it possible to assure the rigidity of the device substrate even when the opening parts are formed in an array. The ultrasonic device can be prevented from being damaged for being handled, and thereby easily handled. In this configuration, interior spaces of the opening parts communicate with the exterior space of the substrate through the ventilation path and the void space. Ventilation is assured between the interior spaces of the opening parts and the exterior space of the substrate. Therefore, the interior spaces of the opening parts are not hermetically closed. The interior spaces of the opening parts easily follow a fluctuation in surrounding pressure. With this configuration, the thin film ultrasonic transducer elements can be securely prevented from being damaged. If the interior spaces of the opening parts are hermetically closed, the thin film ultrasonic transducer elements may be damaged due to the fluctuation in the surrounding pressure.

(8) The ultrasonic device can include a device substrate which defines opening parts individually for the thin film ultrasonic transducer elements and is provided at a first surface thereof with a vibration film closing the opening parts; and a plate member which is attached to a second surface of the device substrate opposite to the first surface of the device substrate, has such an area as to accommodate at least a contour of the element array in a plan view viewed from the thickness direction of the device substrate, and has a through-opening continuing from the opening part. The thin film ultrasonic transducer elements cause the vibration film to perform ultrasonic vibration during transmission of ultrasonic waves. The ultrasonic wave is transmitted to a front side from the vibration film, and output from a first surface of the device substrate. At the same time, the ultrasonic wave is transmitted to a rear side from the vibration film as well. The ultrasonic wave transmits within the opening part. The opening part continues to the through-opening, thereby increasing the length of transmission path of the ultrasonic wave. With the increase in the length of the transmission path, the ultrasonic wave is attenuated. With this configuration, it is possible to suppress the influence of the ultrasonic waves transmitted to the rear side from the vibration film.

(9) The recess part can be provided at the bottom surface thereof with a through-hole which is connected to the through-opening and runs through the substrate. The interior spaces of the opening parts communicate with the exterior space of the substrate through the through-opening and the through-hole. Ventilation is assured between the interior spaces of the opening parts and the exterior space of the substrate. Therefore, the interior spaces of the opening parts are not hermetically closed. The interior spaces of the opening parts easily follow the fluctuation in surrounding pressure. With this configuration, the thin film ultrasonic transducer elements can be securely prevented from being damaged. If the interior spaces of the opening parts are hermetically closed, the thin film ultrasonic transducer elements may be damaged due to the fluctuation in the surrounding pressure.

(10) A ventilation path can be formed between the bottom surface of the recess part and the device substrate so as to be connected to the through-opening and communicate with the void space formed between the lateral surface of the recess part and the ultrasonic device. The interior spaces of the opening parts communicates with the exterior space of the substrate through the through-opening, the ventilation path and the void space. Ventilation is assured between the interior spaces of the opening parts and the exterior space of the substrate. Therefore, the interior spaces of the opening parts are not hermetically closed. The interior spaces of the opening parts easily follow the fluctuation in surrounding pressure. With this configuration, the thin film ultrasonic transducer elements can be securely prevented from being damaged. If the interior spaces of the opening parts are hermetically closed, the thin film ultrasonic transducer elements may be damaged due to the fluctuation in the surrounding pressure.

(11) The ultrasonic device unit can be assembled into a probe so as to be utilized. In this instance, the probe is provided with the ultrasonic device unit, and a housing supporting the ultrasonic device unit.

(12) The ultrasonic device unit can be assembled into an electronic device so as to be utilized. In this instance, the electronic device is provided with the ultrasonic device unit, and a processing unit which is connected to the ultrasonic device unit and processes an output of the ultrasonic device unit.

(13) The ultrasonic device unit can be assembled into an ultrasonic imaging device. In this instance, the ultrasonic imaging device is provided with the ultrasonic device unit, a processing unit which is connected to the ultrasonic device unit and processes an output of the ultrasonic device unit so as to create an image, and a display device for displaying the image.

DESCRIPTION OF EXEMPLARY EMBODIMENTS

The following describes an embodiment of the invention with reference to the attached drawings. The embodiments explained below are not intended to limit improperly the contents of the present invention described in the claims. None of the structural details explained in the embodiments are absolutely necessary for the solution presented by the present invention.

(1) Overall Configuration of an Ultrasonic Diagnosis Device

Figure 1:
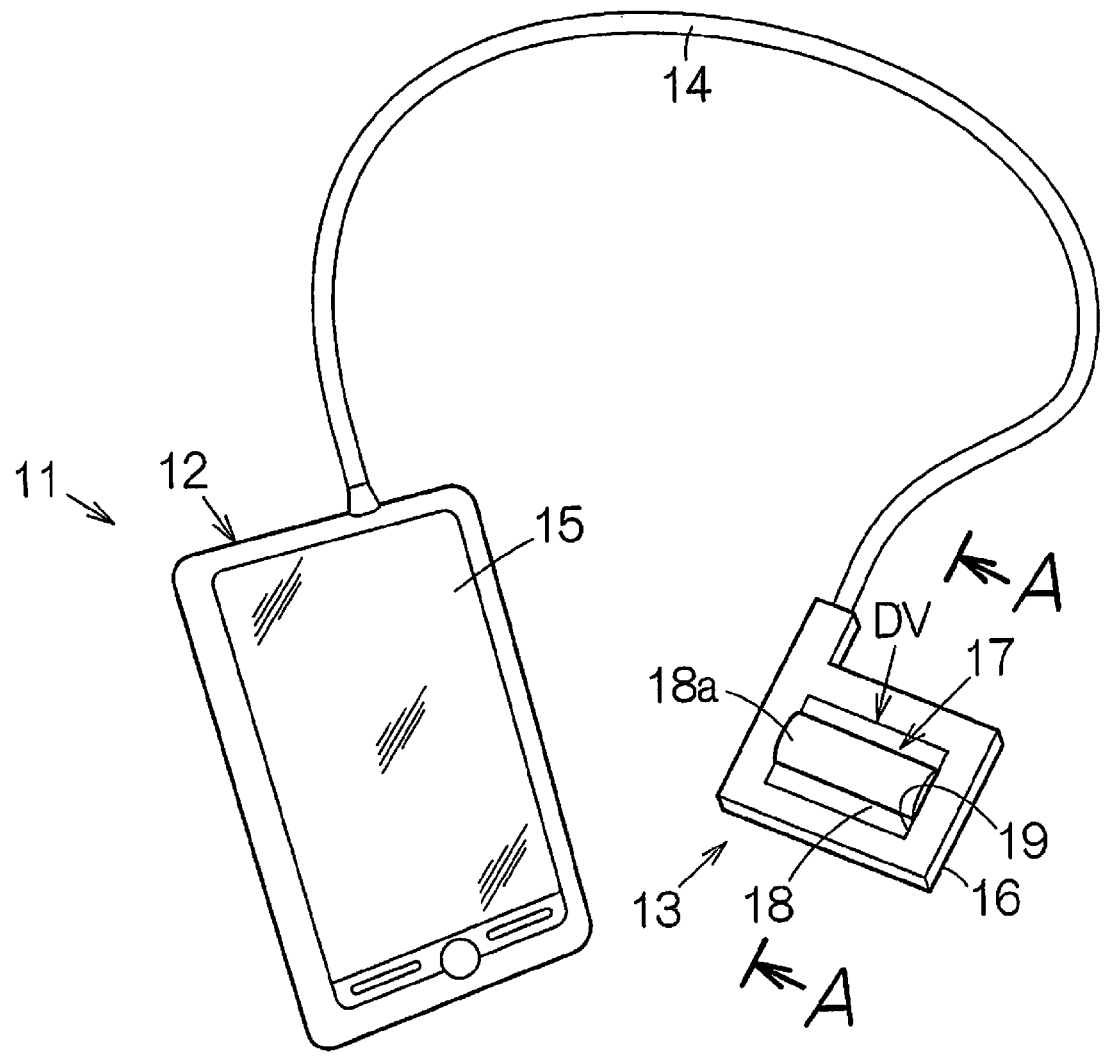
FIG. 1 is an external view schematically showing one specific example of an electronic device, namely an ultrasonic diagnosis device, according to one embodiment.

FIG. 1 schematically shows one specific example of a configuration of an electronic device, namely an ultrasonic diagnosis device (ultrasonic imaging device) 11, according to one embodiment of the present invention. The ultrasonic diagnosis device 11 is provided with a device terminal (processing unit) 12 and an ultrasonic probe (probe) 13. The device terminal 12 and the ultrasonic probe 13 are connected to each other via a cable 14. Electric signals are transmitted through the cable 14 between the device terminal 12 and the ultrasonic probe 13. A display panel (displaying device) 15 is assembled into the device terminal 12. A screen of the display panel 15 is exposed at a surface of the device terminal 12. In the device terminal 12, an image is created on the basis of ultrasonic waves detected with the ultrasonic probe 13. An imaged detection result is displayed on the screen of the display panel 15.

The ultrasonic probe 13 has a housing 16. An ultrasonic device unit DV is accommodated within the housing 16. The ultrasonic device unit DV is provided with an ultrasonic device 17. The ultrasonic device 17 is provided with an acoustic lens 18. The acoustic lens 18 is formed at its external surface into a partially cylindrical surface 18a. The acoustic lens 18 is made of silicone resin, for example. The acoustic lens 18 has an acoustic impedance close to the acoustic impedance of a living body. The housing 16 defines a window hole 19. The acoustic lens 18 is disposed within the window hole 19. The external surface of the acoustic lens 18 is exposed at a surface of the housing 16. The ultrasonic device 17 outputs the ultrasonic wave from its surface and receives a reflection wave of the ultrasonic wave.

Figure 2:
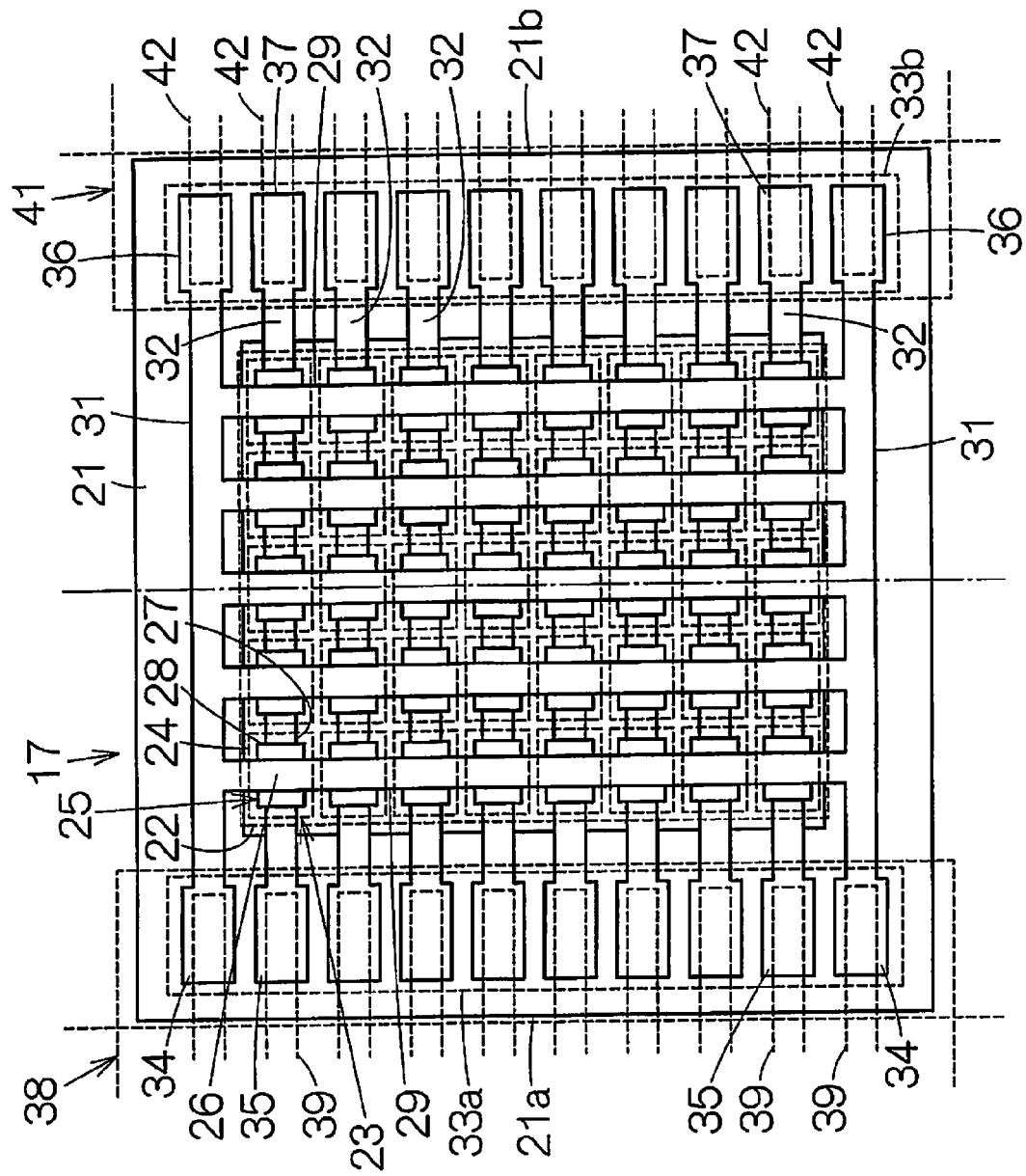
FIG. 2 is an expanded plan view of an ultrasonic device according to one embodiment.

FIG. 2 schematically shows a plan view of the ultrasonic device 17. The ultrasonic device 17 is provided with a base 21. An element array 22 is formed on a surface (first surface) of the base 21. The element array 22 is constituted by an arrangement of thin film ultrasound transducer elements (hereinafter referred to as "elements") 23 arranged in an array. The arrangement is in form of a matrix with a plurality of lines and a plurality of rows. The arrangement may also be established as a zigzag arrangement. In the zigzag arrangement, a group of elements 23 in an even row can be displaced with respect to a group of elements 23 in an odd row by one half of a line pitch. One of the number of the elements in the odd rows and the number of the elements in the even rows may be lower than the other by one.

Each element 23 is provided with a vibration film 24. In FIG. 2, the contour of each vibration film 24 is depicted as a dotted line in a plan view in a direction perpendicular to a film surface of the vibration film 24 (a plan view in a thickness direction of a substrate). A piezoelectric element 25 is formed on the vibration film 24. The piezoelectric element 25 is composed of a top electrode (electrode) 26, a bottom electrode (electrode) 27 and a piezoelectric film (piezoelectric body) 28. The piezoelectric film 28 is interposed between the top electrode 26 and the bottom electrode 27 at each element 23. The bottom electrode 27, the piezoelectric film 28 and the top electrode 26 are layered in this order. The supersonic device 17 is formed as a single ultrasonic transducer element chip (substrate).

A plurality of first electric conductors 29 is formed on the surface of the base 21. The first electric conductors 29 extend in parallel to each other in a line direction of the arrangement. One first electric conductor 29 is assigned to each line of elements 23. One first electric conductor 29 is connected commonly to the piezoelectric body films 28 of the elements 23 arranged in a line direction of the arrangement. The first electric conductor 29 forms the top electrode 26 for each of the elements 23. Both ends of the first electric conductor 29 are connected to a pair of extension wires 31. The extension wires 31 extend in parallel to each other in a row direction of the arrangement. Accordingly, all of the first electric conductors 29 have the same length. In this way, the top electrodes 26 are connected commonly to the elements 23 in the overall matrix. The first electric conductor 29 can be formed of iridium (Ir), for example. It is also possible to use another electrically conductive material as the first electric conductor 29.

A plurality of second electric conductors 32 is formed on the surface of the base 21. The second electric conductors 32 extend in parallel to each other in a row direction of the arrangement. One second electric conductor 32 is assigned to each row of the elements 23. One second electric conductor 32 is disposed commonly to the piezoelectric films 28 of the elements 23 arranged in the row direction of the arrangement. The second electric conductor 32 forms the bottom electrode 27 for each element 23. For example, a laminate of titanium (Ti), iridium (Ir), platinum (Pt) and titanium (Ti) can be utilized for the second electric conductor 32. It is also possible to use another electrically conductive material as the second electric conductor 32.

It is possible to switch the electrical connection of the elements 23 for each row. In response to the switch of the electrical connection, it is possible to achieve a linear scan and a sector scan. Since the elements 23 in a single row can output ultrasonic waves simultaneously, the number of single lines, that is, the number of lines of the arrangement can be set depending on the output level of the ultrasonic wave. The number of lines can be set in a range of 10 to 15, for example. In the figures, some lines are not shown, and only five lines are shown. The number of rows of the arrangement can be set depending on the extent of a scan range. The number of rows can be set to 128 or 256, for example. In the figures, some rows are not shown, and only eight rows are shown. The functions of the top electrode 26 and the bottom electrode 27 can be reversed. That is, the bottom electrodes can be connected commonly to the elements 23 of overall matrix, while the top electrodes can be connected commonly to the elements 23 for each row of the arrangement.

The contour of the base 21 has a first side 21a and a second side 21b, which are defined by a pair of mutually parallel lines and face each other. A first terminal array 33a is disposed as a single line between the first side 21a and a contour of the element array 22. A second terminal array 33b is disposed as a single line between the second side 21b and a contour of the element array 22. The first terminal array 33a can form one line parallel to the first side 21a. The second terminal array 33b can form one line parallel to the second side 21b. The first terminal array 33a is constituted by a pair of top electrode terminals 34 and a plurality of bottom electrode terminals 35. Similarly, the second terminal array 33b is constituted by a pair of top electrode terminals 36 and a plurality of bottom electrode terminals 37. The two ends of each one extension wire 31 are respectively connected to the top electrode terminals 34, 36. The extension wire 31 and the top electrodes 34, 36 can be formed plane-symmetrically in relation to a perpendicular plane bisecting the element array 22. The two ends of one second electric conductor 32 are respectively connected to the bottom electrode terminals 35, 37. The second electric conductor 32 and the bottom electrode terminals 35, 37 can be formed plane-symmetrically in relation to a perpendicular plane bisecting the element array 22. Herein, the contour of the base 21 has a rectangular shape. The contour of the base 21 may also be square or trapezoidal.

A first flexible printed circuit board (hereinafter referred to as "first circuit board") 38 is connected to the base 21. The first circuit board 38 covers the first terminal array 33a. The first circuit board 38 is provided at its one end with electrically conductive lines, namely first signal lines 39 that respectively correspond to the top electrode terminals 34 and the bottom electrode terminals 35. The first signal lines 39 are respectively connected so as to face the top electrode terminals 34 and the bottom electrode terminals 35. Similarly, a second flexible printed circuit board (hereinafter referred to as "second circuit board") 41 covers the base 21. The second circuit board 41 covers the second terminal array 33b. The second circuit board 41 is provided at its one end with electrically conductive lines, namely second signal lines 42 that respectively correspond to the top electrode terminals 36 and the bottom electrode terminals 37. The second signal lines 42 are respectively connected so as to face the top electrode terminals 36 and the bottom electrode terminals 37.

(2) Configuration of the Ultrasonic Device Unit According to a First Embodiment

Figure 3:
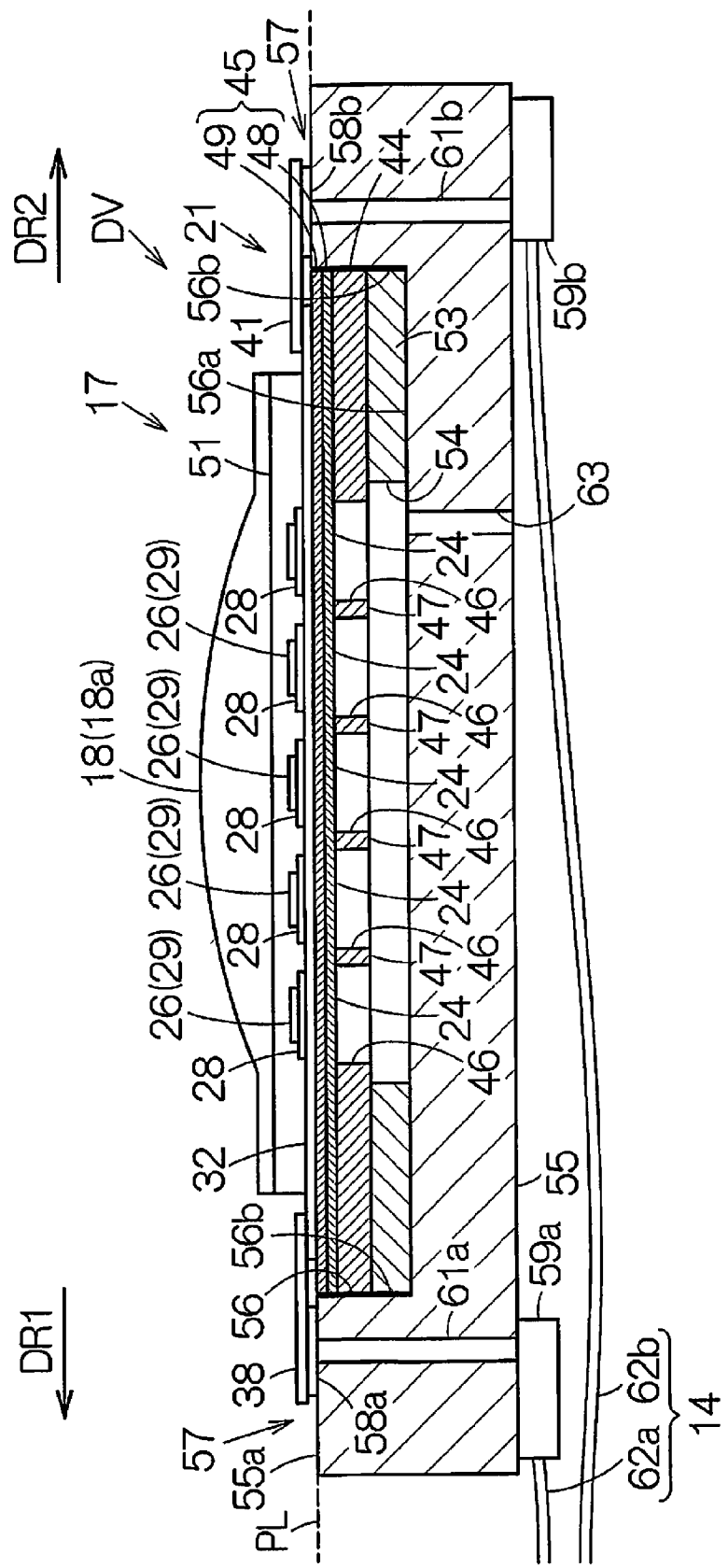
FIG. 3 is a cross-sectional view of an ultrasonic device unit according to a first embodiment taken along line A-A in FIG. 1.

As shown in FIG. 3, the base 21 is provided with a substrate (device substrate) 44 and a cover film 45. The cover film 45 is formed over the entire surface of the substrate 44. The substrate 44 is provided with an opening part 46 for each element 23. The opening parts 46 are disposed in array form in the substrate 44. Each opening part 46 opens at a surface (second surface) on the rear side (opposite side) of the corresponding element 23. A contour of a region in which the opening parts 46 are disposed corresponds to a contour of the element array 22. A partitioning wall 47 is disposed between every two adjacent opening parts 46. The wall thickness of the partitioning wall 47 corresponds to an interval between the opening parts 46. The partitioning wall 47 defines two wall surfaces within planes which extend in parallel to each other. The wall thickness corresponds to a distance between the two wall surfaces. That is, the wall thickness can be defined by a length of a normal line which is orthogonal to the wall surfaces and interposed between the wall surfaces. The substrate 44 is formed of a silicon substrate, for example.

The cover film 45 is made of a silicon oxide ($SiO_2$) layer 48 layered on a surface of the substrate 44 and a zirconium oxide ($ZrO_2$) layer 49 layered on a surface of the silicon oxide layer 48. The cover film 45 closes the spaces of the opening parts 46. In this configuration, a portion of the cover film 45 forms the vibration film 24, in correspondence with the contour of the opening part 46. The vibration film 24 is that portion of the cover film 45 that is exposed through the opening part 46, and that is capable of vibrating in the thickness direction of the substrate 44. The film thickness of the silicon oxide layer 48 may be set according to the resonance frequency.

The bottom electrode 27, the piezoelectric body film 28 and the top electrode 26 are layered in this order on a surface of the vibration film 24. The piezoelectric film 28 can be made of lead zirconate titanate (PZT), for example. It is also possible to use another piezoelectric material as the piezoelectric film 28. The piezoelectric film 28 covers the second electric conductor 32 completely under the first electric conductor 29. With the function of the piezoelectric film 28, it is possible to prevent short-circuits between the first electric conductor 29 and the second electric conductor 32.

An acoustic matching layer 51 is layered on the surface of the base 21. The acoustic matching layer 51 covers the element array 22. The thickness of the acoustic matching layer 51 is determined according to the resonance frequency of the vibration film 24. For example, a silicone resin film can be used for the acoustic matching layer 51. An acoustic lens 18 is disposed on the acoustic matching layer 51. The acoustic lens 18 is intimately adhered at a planar surface in a rear side of the partially cylindrical surface 18a to the surface of the acoustic matching layer 51. The acoustic lens 18 is adhered to the base 21 with the function of the acoustic matching layer 51. The generatrix of the partially cylindrical surface 18a is positioned parallel to the first electric conductor 29. The curvature of the partially cylindrical surface 18a is determined in accordance with a focus point of the ultrasonic waves transmitted from the elements 23 in a single row connected to the second conductors 33 in a single line.

A reinforcing plate (plate member) 53 is coupled as a backing material to the rear surface of the base 21. The reinforcing plate 53 is formed into a planar plate. The rear surface of the base 21 is superimposed on a surface of the reinforcing plate 53. A through-opening 54 is formed in the reinforcing plate 53. The surface of the reinforcing plate 53 is adhered to the rear surface of the base 21. For this adhesion, the reinforcing plate 53 may be adhered to the base 21 with an adhesive. The reinforcing plate 53 reinforces the rigidity of the base 21. With the function of the reinforcing plate 53, the base 21 can be assured to have a surface with good planarity. The reinforcing plate 53 can be provided with a rigid base material, for example. The rigid base material may be formed of a metal material such as 42 alloy (iron nickel alloy), for example.

The through-opening 54 has such an extent that allows it to accommodate at least the contour of the element array 22 in a plan view viewed from the thickness direction of the base 21. The through-opening 54 continues from the opening parts 46 of the elements 23 included in the element array 22. The opening parts 46 and the through-opening 54 are filled with air. The thickness of air from the vibration film 24 is set to an odd multiple of a quarter of a wavelength $\lambda$ ($\lambda/4$) of ultrasonic wave. The thickness of air can be set on the basis of the thicknesses of the substrate 44 and the reinforcing plate 53.

The ultrasonic device unit DV is provided with a wiring substrate 55. The wiring substrate 55 is coupled to the ultrasonic device 17. The wiring substrate 55 has a planar part 55a extending on a plane PL and a recess part 56 recessed from the planar part 55a. The recess part 56 is shaped into the contour of the base 21 in a plan view. The recess part 56 is sectioned into a bottom surface 56a extending in parallel to the plane PL and a wall surface 56b erected perpendicularly from the bottom surface 56a at the contour of the bottom surface 56a. The ultrasonic device 17 is received by the recess part 56. The surface of the cover film 45 is superimposed on the plane PL of the wiring substrate 55. With this configuration, the ultrasonic device 17 is mounted such that its surface is flush with the plane PL. The ultrasonic device 17 may be fixed to the wiring substrate 55 with a resin material. Compared to the case that the ultrasonic device 17 is mounted on the plane PL of the wiring substrate 55, it is possible to reduce the thickness of the ultrasonic device unit DV. The surface of the cover film 45 corresponds to the output surface of the ultrasonic wave of the elements 23, and is positioned at an array surface.

The wiring substrate 55 is provided with a wiring pattern 57. The first circuit board 38 and the second circuit board 41 of the ultrasonic device 17 is connected to the wiring pattern 57. The wiring pattern 57 is provided with first electrically conductive pads (terminals) 58a and second electrically conductive pads (terminals) 58b. The first electrically conductive pads 58a and the second electrically conductive pads 58b are formed on the plane PL of the wiring substrate 55. The first electrically conductive pads 58a and the second electrically conductive pads 58b are disposed individually so as to be correspondent with the first signal lines 39 and the second signal lines 42, respectively. The first electrically conductive pads 58a and the second electrically conductive pads 58b are made of an electrically conductive material such as copper, for example. The corresponding first signal lines 39 and the corresponding second signal lines 42 are connected to the first electrically conductive pads 58a and the second electrically conductive pads 58b, respectively.

One end of the first circuit board 38 is superimposed on the planar part 55a of the ultrasonic device 17 at a higher position than the plane PL of the wiring substrate 55 and connected to the same. The first circuit board 38 extends in a first direction DR1 from one end on the ultrasonic device 17. The other end of the first circuit board 38 is superimposed on the planar part 55a of the wiring substrate 55 and connected to the same. The first circuit board 38 is superimposed so as to interpose the first electrically conductive pads 58a between the first circuit board 38 and the plane PL. Similarly, one end of the second circuit board 41 is superimposed on the planar part 55a of the ultrasonic device 17 at a higher position than the plane PL of the wiring substrate 55 and connected to the same. The second circuit board 41 extends in a second direction DR2 from one end on the ultrasonic device 17. The second direction DR2 is opposite to the first direction DR1. The other end of the second circuit board 41 is superimposed on the planar part 55a of the wiring substrate 55 and connected to the same. The second circuit board 41 is superimposed so as to interpose the second electrically conductive pads 58b between the second circuit board 41 and the plane PL. The ultrasonic device 17 is mounted such that its surface is flush with the plane PL, and it is possible to prevent the first circuit board 38 and the second circuit board 41 from bending.

A first connector 59a and a second connector 59b are disposed on the rear surface of the wiring substrate 55. The first connector 59a is connected to the first electrically conductive pads 58a with a via 61a. The second connector 59b is connected to the second electrically conductive pads 58b with a via 61b. The vias 61a, 61b run from the front surface to the rear surface of the wiring substrate 55. The cable 14 is formed of wires 62a, 62b, which are connected respectively to the first connector 59a and the second connector 59b.

The wiring substrate 55 is provided at its recess part 56 with a through-hole 63. The through-hole 63 is positioned at the bottom surface 56a of the recess part 56, and runs through the wiring substrate 55. The through-hole 63 is connected at the bottom surface 56a of the recess part 56 to the through-opening 54 of the ultrasonic device 17. The spaces of the opening parts 46 of the ultrasonic device 17 communicate with an exterior space of the wiring substrate 55 via the through-opening 54 and the through-hole 63.

Figure 4:
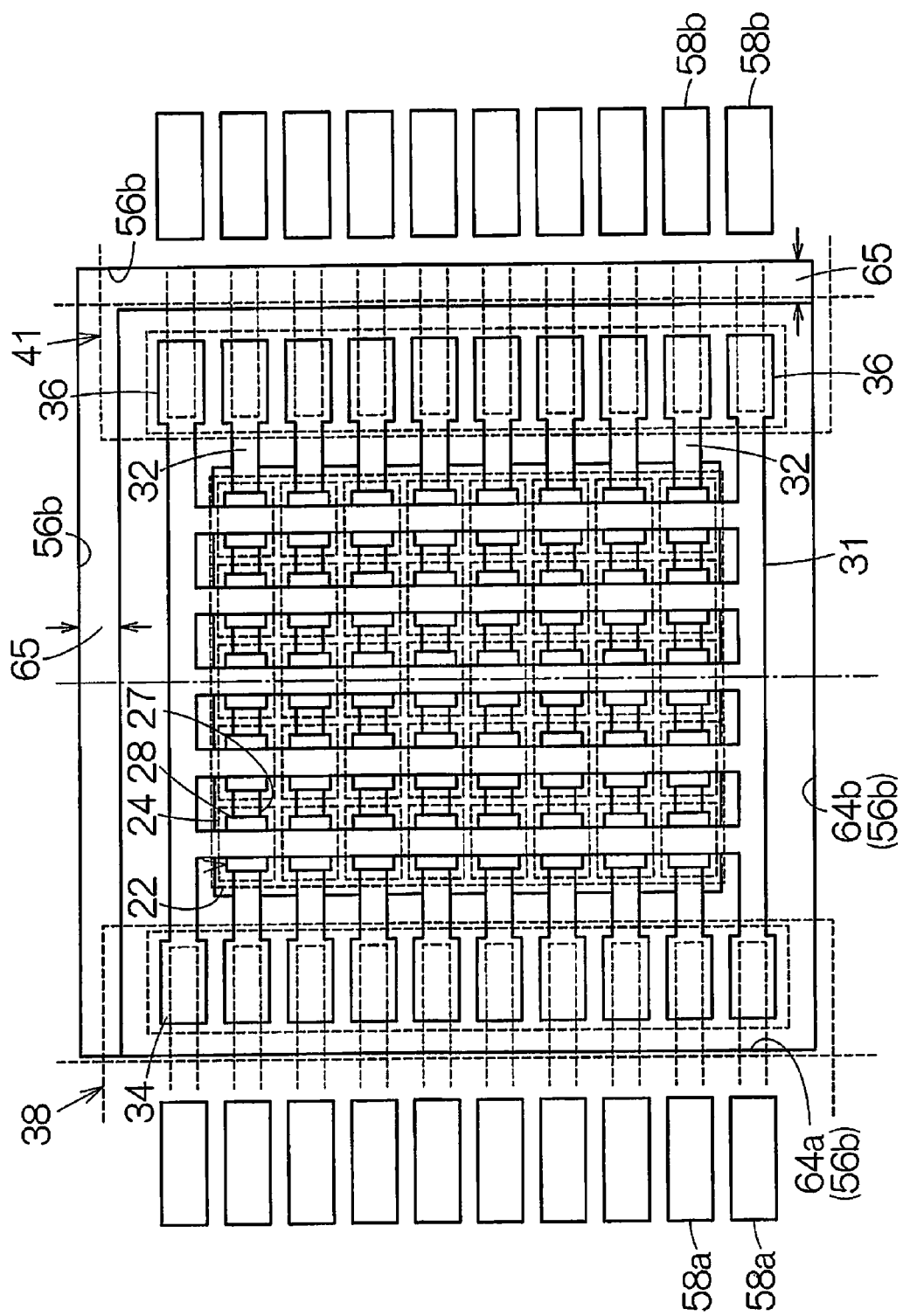
FIG. 4 is a plan view of the ultrasonic device unit.

As shown in FIG. 4, the recess part 56 has wall surfaces (lateral surfaces) 56b (64a, 64b) partitioned by two perpendicular surfaces intersecting mutually. The two wall surfaces 64a, 64b are orthogonal to each other. A lateral surface of ultrasonic device 17 abuts against the two wall surfaces 64a, 64b so as to come into contact with the same. Accordingly, the top electrode terminals 34, 36 and the bottom electrode terminals 35, 37 on the base 21 are positioned in relation to the two wall surfaces 64a, 64b. The first electrically conductive pads 58a and the second electrically conductive pads 58b are positioned in relation to the two wall surfaces 64a, 64b, in advance. Herein, a void space 65 is formed between the ultrasonic device 17 and the rest of the wall surface 56b. A resin material may be disposed in the void space 65 in order to fix the ultrasonic device 17.

(3) Operation of Ultrasonic Diagnosis Device

Next, the operation of the ultrasonic diagnosis device 11 will be briefly explained. For the transmission of ultrasonic waves, a pulse signal is supplied to the piezoelectric element 25. The pulse signal is supplied to the elements 23 for each row via the bottom electrode terminals 35, 37 and the top electrode terminals 34, 36. An electric field acts on the piezoelectric film 28 between the bottom electrode 27 and the top electrode 26 in each element 23. The piezoelectric film 28 vibrates at an ultrasonic frequency. The vibration of the piezoelectric film 28 is transmitted to the vibration film 24. With this configuration, the vibration film 24 performs an ultrasonic wave vibration. As a result, a desired ultrasonic beam is transmitted towards on an object to be detected (for example, the interior of a human body).

The reflected wave of the ultrasonic wave vibrates the vibration film 24. The ultrasonic vibration of the vibration film 24 causes the piezoelectric film 28 to perform ultrasonic vibration at a desired frequency. In response to the piezoelectric effect of the piezoelectric element 25, the piezoelectric element 25 outputs an electric voltage. In each element 23, an electric potential is generated between the top electrode 26 and the bottom electrode 27. The electric potential is output as an electric signal from the bottom electrode terminals 35, 37 and the top electrode terminals 34, 36. With this configuration, it is possible to detect ultrasonic waves.

The ultrasonic wave is repetitively transmitted and received. As a result, it is possible to achieve a linear scan and a sector scan. After completion of the scan, an image is created on the basis of a digital output signal. The created image is displayed on a screen of the display panel 15.

As described above, the ultrasonic device 17 is received by the recess part 56. The ultrasonic device 17 is disposed on the portion of the wiring substrate 55 that is recessed from the plane PL. The first circuit board 38 and the second circuit board 41 are superimposed on the ultrasonic device 17 disposed in the recessed portion and connected to the same. Accordingly, compared to the case that the ultrasonic device 17 is mounted on the plane PL of the wiring substrate 55, it is possible to suppress the bending of the first circuit board 38 and the second circuit board 41. AS the length of the flexible printed circuit board decreases relative to its width, it is possible to prevent the flexible printed circuit board from bending. And as the flexible printed circuit board is kept from bending, it is possible to shorten the lengths of the first circuit board 38 and the second circuit board 41 for connection of the first circuit board 38 and the second circuit board 41. With this configuration, it is possible to securely miniaturize the ultrasonic device unit DV.

In the wiring substrate 55, the wall surfaces 64a, 64b of the recess part 56 are precisely positioned in relation to the first electrically conductive pads 58a and the second electrically conductive pads 58b on the plane PL. Accordingly, it is possible to precisely position the ultrasonic device 17 in relation to the first electrically conductive pads 58a and the second electrically conductive pads 58b on the plane PL, when the ultrasonic device 17 received by the recess part 56 abuts against the two wall surfaces 64a, 64b. With this configuration, it is possible to realize the secure connection of the first circuit board 38 and the second circuit board 41 in relation to the wiring substrate 55 and the ultrasonic device 17. For fabrication of the ultrasonic device unit DV, it is possible to connect the first circuit board 38 and the second circuit board 41 to the top electrode terminals 34, 36 and the bottom electrode terminals 35, 37 on the ultrasonic device 17 as well as the first electrically conductive pads 58a and the second electrically conductive pads 58b on the wiring substrate 55 after the ultrasonic device 17 is fixed within the recess part 56. Instead, it is possible to connect the first circuit board 38 and the second circuit board 41 to the first electrically conductive pads 58a and the second electrically conductive pads 58b on the wiring substrate 55 while the ultrasonic device 17 abuts against the wall surfaces 64a, 64b of the recess part 56 after the first circuit board 38 and the second circuit board 41 are connected to the top electrode terminals 34, 36 and the bottom electrode terminals 35, 37 on the ultrasonic device 17. Meanwhile, if the ultrasonic device 17 were disposed on the plane PL without being provided with an abutted object, the ultrasonic device 17 could not be precisely positioned in relation to the first electrically conductive pads 58a and the second electrically conductive pads 58b on the wiring substrate 55. As a result, the first circuit board 38 and the second circuit board 41 could not be precisely positioned in relation to the first electrically conductive pads 58a and the second electrically conductive pads 58b on the wiring substrate 55 before being adhered to the ultrasonic device 17 in advance.

As described above, the first circuit board 38 is superimposed on the plane PL and the ultrasonic device 17 which is mounted so as to be flush with the plane PL. The first circuit board 38 can be prevented from bending. It is possible to minimize the length of the first circuit board 38 for connection of the first circuit board 38. With this configuration, it is possible to securely miniaturize the ultrasonic device unit DV. In such an ultrasonic device unit DV, the first circuit board 38 can be positioned only by in-plane displacement, thereby making it possible to connect the first circuit board 38 to the ultrasonic device 17 and the wiring substrate 55 after the ultrasonic device 17 is fixed to the wiring substrate 55. Herein, the first circuit board 38 extends over the wall surface 64a of the recess part 56. Accordingly, the first circuit board 38 prevents the ultrasonic device 17 from being abutted against the wall surface 64a.

The first circuit board 38 extends in the first direction DR1 from the ultrasonic device 17. The second circuit board 41 extends in the second direction DR2 opposite to the first direction DR1 from the ultrasonic device 17. For use of the ultrasonic device unit DV, the ultrasonic device 17 is pressed to an object to be detected. For example, when the ultrasonic device 17 is displaced along the surface of the object to be detected in the first direction DR1, a shearing force acts on the ultrasonic device 17 in the second direction DR2. In this situation, the first circuit board 38 is subjected to a tensile force. The first circuit board 38 prevents the ultrasonic device 17 from being displaced while resisting to the tensile force. In contrast, when the ultrasonic device 17 is displaced along the surface of the object to be detected in the second direction DR2, a shearing force acts on the ultrasonic device 17 in the first direction DR1. In this situation, the second circuit board 41 is subjected to a tensile force. The second circuit board 41 prevents the ultrasonic device 17 from being displaced while resisting to the tensile force. With this configuration, it is possible to prevent the ultrasonic device 17 from being displaced in relation to the wiring substrate 55.

Figure 5:
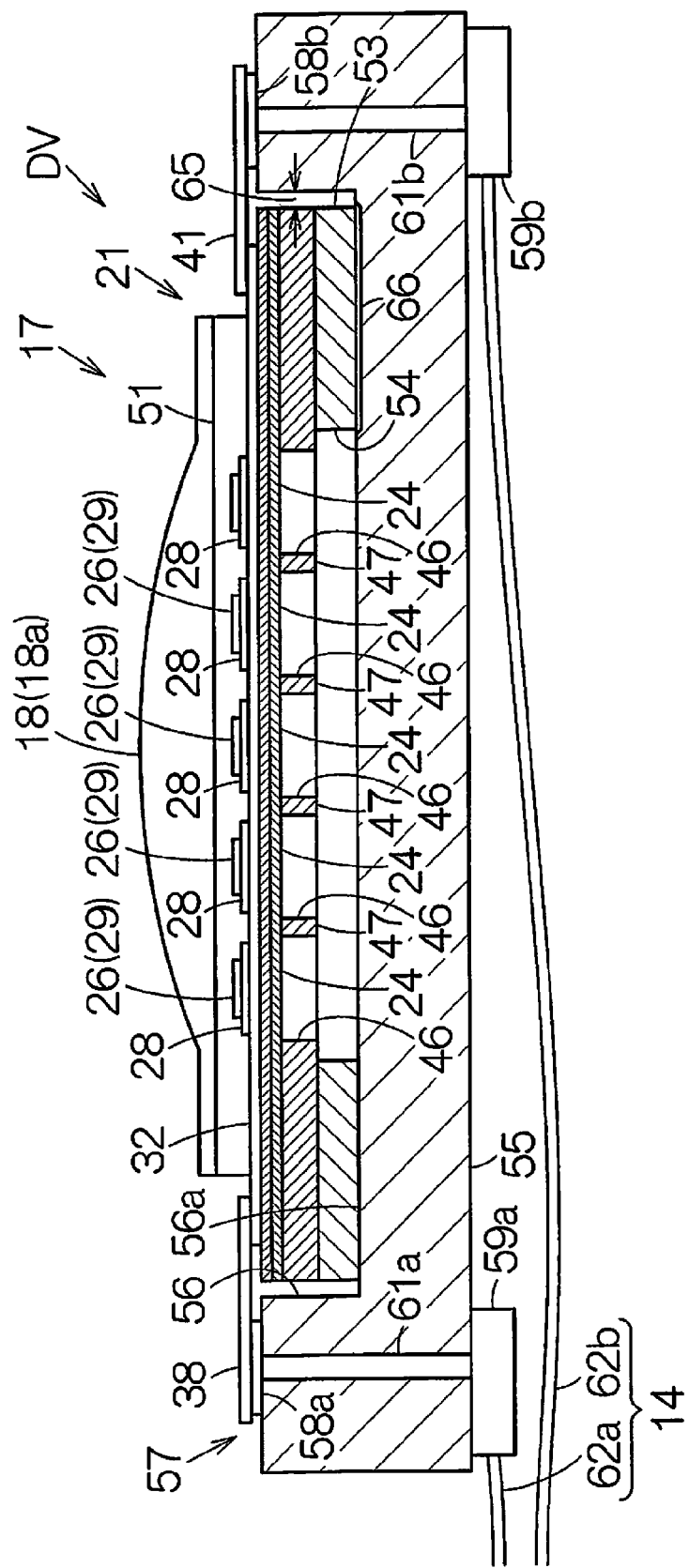
FIG. 5, which corresponds to FIG. 3, is a cross-sectional view of the ultrasonic device unit according to a modification example of the first embodiment.

When the element 23 causes the vibration film 24 to perform ultrasonic vibration during the transmission of ultrasonic waves, the ultrasonic waves are transmitted to a front side from the vibration film 24 so as to be output from a first surface of the substrate 44. In this situation, the ultrasonic waves are transmitted to a rear side from the vibration film 24 as well. The ultrasonic waves transmit within the opening parts 46. The opening parts 46 continue to the through-opening 54, thereby increasing a length of ultrasonic wave transmission path. The increase in the length of transmission path causes ultrasonic waves to attenuate. With this configuration, it is possible to reduce the influence of the ultrasonic waves transmitted to the rear side from the vibration film 24. Interior spaces of the opening parts 46 communicate with an exterior space of the wiring substrate 55 through the through-opening 54 and the through-hole 63. It is possible to assure air flow between the interior spaces of the opening parts 46 and the exterior space of the wiring substrate 55. Therefore, the interior spaces of the opening parts 46 are not hermetically closed. The interior spaces of the opening parts 46 easily follow a fluctuation in surrounding pressure. With this configuration, it is possible to securely prevent the elements 23 from being damaged. If the interior spaces of the opening parts 46 were hermetically closed, the element 23 might be damaged due to the pressure fluctuation. For connection of the interior spaces of the opening parts 46 with the exterior space of the wiring substrate 55, as shown in FIG. 5, for example, a ventilation path (ventilation route) 66 can be formed between the reinforcing plate 53 of the ultrasonic device 17 and the bottom surface 56a of the recess part 56 instead of the through-hole 63. The ventilation path 66 is connected to the through-opening 54, and communicates with the void space 65 formed between the wall surface 56b of the recess part 56 and the ultrasonic device 17. For formation of the ventilation path 66, a groove can be provided to at least one of the bottom surface 56a of the recess part 56 and the rear surface of the reinforcing plate 53. With this configuration, it is possible to communicate the interior spaces of the opening parts 46 with the exterior space of the wiring substrate 55 through the through-opening 54, the ventilation path 66 and the void space 65.

(4) Configuration of Ultrasonic Device Unit According to a Second Embodiment

Figure 6:
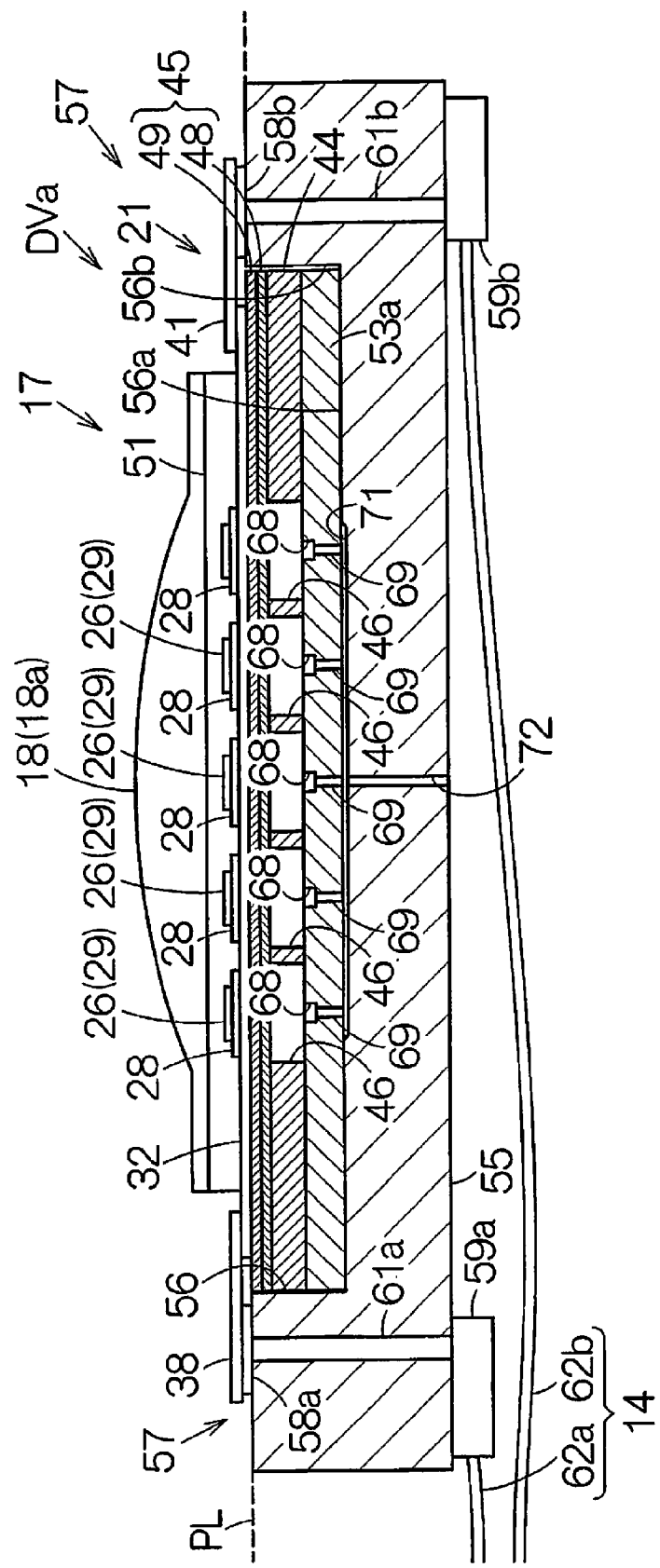
FIG. 6, which corresponds to FIG. 3, is a cross-sectional view of the ultrasonic device unit according to a second embodiment.

FIG. 6 schematically shows a configuration of an ultrasonic device unit DVa according to a second embodiment. In the ultrasonic device unit DVa, the reinforcing plate (plate member) 53a is formed as a continuous plate. That is to say, the through-opening 54 is not formed. The reinforcing plate 53a closes the opening parts 46 from the rear surface of the base 21. Herein, a plurality of linear grooves 68 are disposed in the surface of the reinforcing plate 53a. The grooves 68 partition the surface of the reinforcing plate 53a into a plurality of planes. Each groove 68 forms a single ventilation path commonly for the corresponding lines of the element array 22, for example. The ventilation path is connected to the opening parts 46 in one line. The cross-sectional shape of the groove 68 may be quadrangle, triangle, hemicycle or another.

In the reinforcing plate 53a, a longitudinal hole (ventilation path) 69 is formed for each groove 68. The longitudinal holes 69 are connected to spaces of the grooves 68, and open at the rear surface of the reinforcing plate 53a. A ventilation storage 71 is formed at the bottom surface 56a of the recess part 56, in correspondence with the plurality of longitudinal holes 69. The ventilation storage 71 is formed at a recess which is formed in the bottom surface 56a of the recess part 56, for example. The opening of the longitudinal hole 69 is connected to the ventilation storage 71. The ventilation storage 71 is connected to one through-hole 72, for example. The through-hole 72 is formed in the bottom surface 56a of the recess part 56 and runs through the wiring substrate 55.

In the ultrasonic device unit DVa, the substrate 44 is reinforced with the reinforcing plate 53a, making it possible to assure the rigidity of the ultrasonic device 17 even when the opening parts 46 are formed in an array. For handling, it is possible to prevent the ultrasonic device 17 from being damaged. With this arrangement, it is possible to easily handle the ultrasonic device 17. In this configuration, the interior spaces of the opening parts 46 communicate with the exterior space of the wiring substrate 55 through the grooves 68, the longitudinal holes 69, the ventilation storage 71 and the through-hole 72. It is possible to assure the ventilation between the interior spaces of the opening parts 46 and the exterior space of the wiring substrate 55. Accordingly, the interior spaces of the opening parts 46 are not hermetically closed. The interior spaces of the opening parts 46 easily follow the fluctuation in the surrounding pressure, thereby making it possible to securely prevent the elements 23 from being damaged. Other structures are same as those of the above ultrasonic device unit DV.

(5) Configuration of Ultrasonic Device Unit According to a Third Embodiment

Figure 7:
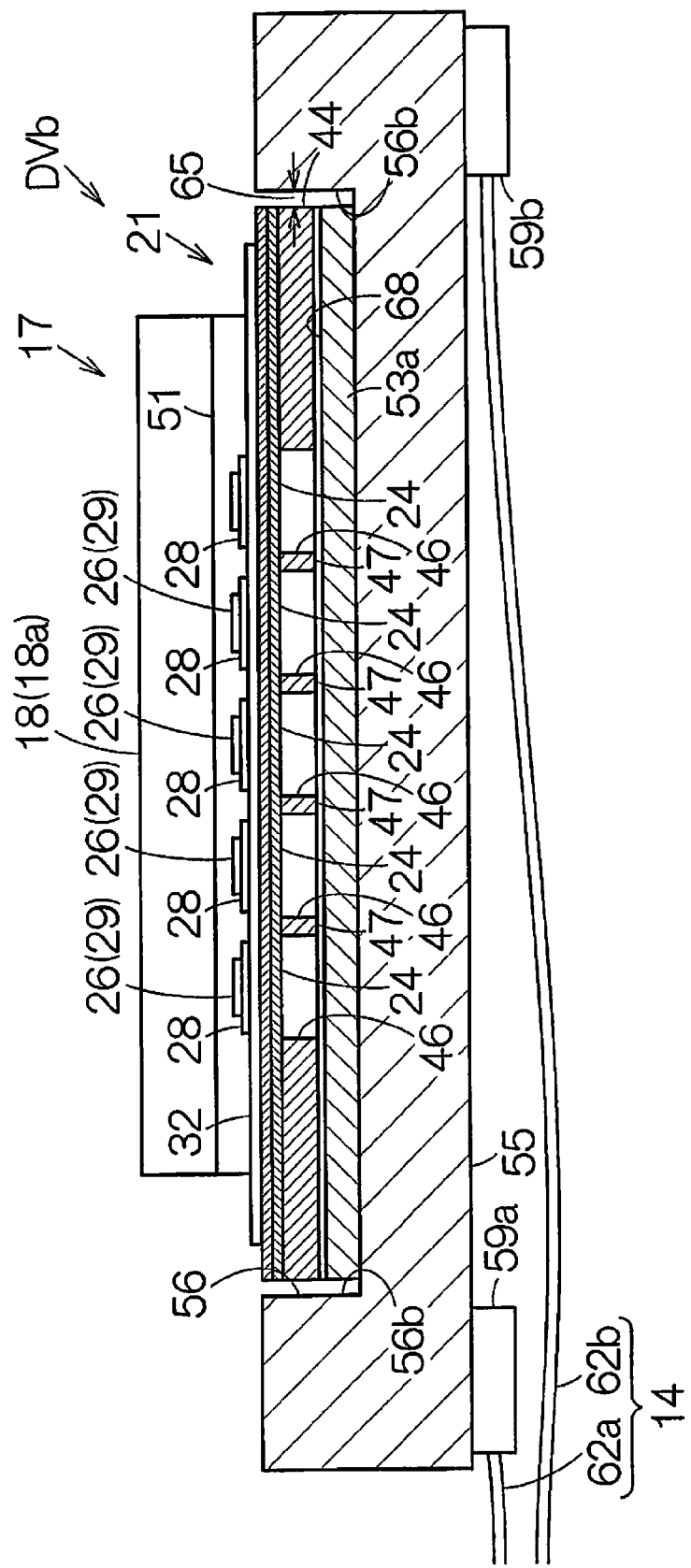
FIG. 7, which corresponds to FIG. 3, is a cross-sectional view of the ultrasonic device unit according to a third embodiment.

FIG. 7 schematically shows a configuration of an ultrasonic device unit DVb according to a third embodiment. In the ultrasonic device unit DVa, the reinforcing plate (plate member) 53a is formed as a continuous plate. That is to say, the through-opening 54 is not formed. The reinforcing plate 53a closes the opening parts 46 from the rear surface of the base 21. Herein, a plurality of linear grooves 68 are disposed in the surface of the reinforcing plate 53a. The grooves 68 partition the surface of the reinforcing plate 53a into a plurality of planes. The groove 68 forms a single ventilation path commonly for each row of the element array 22, for example. Each ventilation path is connected to the opening parts 46 in one row. The cross-sectional shape of the groove 68 may be quadrangular, triangular, hemicyclical or any other shape. Both ends of the groove 68 open at end surfaces of the reinforcing plate 53a facing the wall surface 56b of the recess part 56. With this configuration, the ventilation path of the groove 68 is connected to the void space 65.

The substrate 44 is reinforced with the reinforcing plate 53a, making it possible to assure the rigidity of the ultrasonic device 17 even when the opening parts 46 are formed in an array. For handling, it is possible to prevent the ultrasonic device 17 from being damaged. With this arrangement, it is possible to easily handle the ultrasonic device 17. In this configuration, the interior spaces of the opening parts 46 communicate with the exterior space of the wiring substrate 55 through ventilation paths of the grooves 68 and the void space 65. It is possible to assure the ventilation between the interior spaces of the opening parts 46 and the exterior space of the wiring substrate 55. Accordingly, the interior spaces of the opening parts 46 are not hermetically closed. The interior spaces of the opening parts 46 easily follow the fluctuation in the surrounding pressure, thereby making it possible to securely prevent the elements 23 from being damaged. Other structures are the same as those of the above ultrasonic device unit DV.

(6) Configuration of Ultrasonic Device Unit According to a Fourth Embodiment

Figure 8:
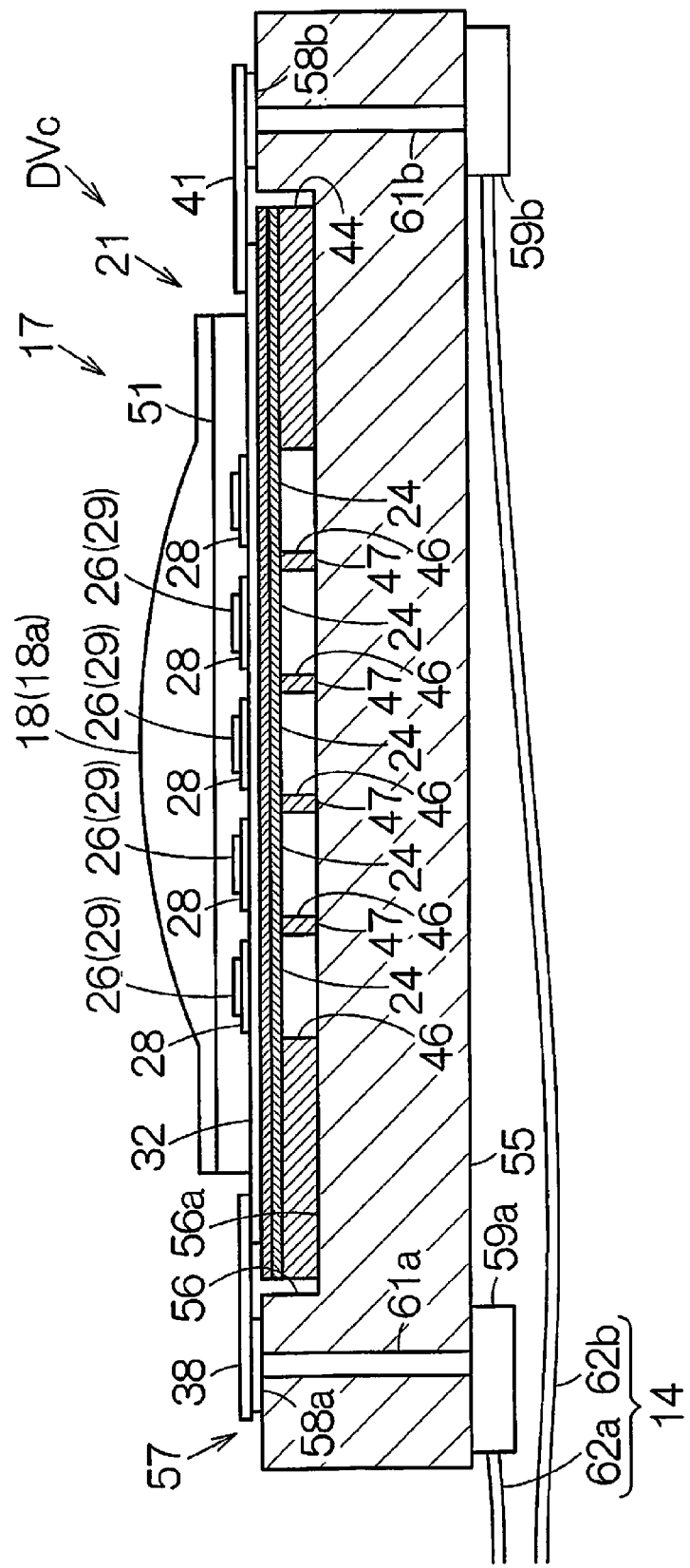
FIG. 8, which corresponds to FIG. 3, is a cross-sectional view of the ultrasonic device unit according to a fourth embodiment.

FIG. 8 schematically shows a configuration of an ultrasonic device unit DVc according to a fourth embodiment. In the ultrasonic device unit DVc, the abovementioned reinforcing plates 53, 53a are not formed. The bottom surface 56a of the recess part 56 is directly adhered to the rear surface of the substrate 44. The opening parts 46 of the substrate 44 are closed with the bottom surface 56a of the recess part 56, making it possible to further miniaturize the ultrasonic device unit DVc. In this configuration, the recess part 56 may be provided with the ventilation storage 71 and the through-hole 72 which are connected to the opening part 46 as described above. The ventilation path may be formed to be connected with the opening part 46 so as to communicate with the void space 65. With this configuration, it is possible to communicate the interior spaces of the opening parts 46 with the exterior space of the wiring substrate 55. Other structures are same as those of the above ultrasonic device unit DV.

In any of the ultrasonic device units DV, DVa, DVb, Dvc, the depth of the recess part 56 may be equal to or less than the thickness of the ultrasonic device 17. When the depth of the recess part 56 is set to be less than the thickness of the ultrasonic device 17, the array surface of the ultrasonic device 17 is positioned to be far away from the bottom surface 56a of the recess part 56 and higher than the plane PL.

Although some embodiments of the invention have been described above in detail, those skilled in the art will readily understand that various modifications may be made without substantially departing from the new items and the effects of the invention. Therefore, such modifications are entirely included within the scope of the invention. For example, any term described at least once together with a broader or synonymous different term in the specification or the drawing may be replaced by the different term at any place in the specification or the drawings. Besides, configurations and operations of the ultrasonic diagnosis device 11, the terminal device 12, the ultrasonic probe 13, the display panel 15, the housing 16, the base 21, the elements 23, the first and second circuit boards 38, 41, the acoustic matching layer 51, the acoustic lens 52 and so forth are not limited to those described in the present embodiment, but may be modified in various ways.

The entire disclosure of Japanese Patent Application No. 2014-058546, filed on Mar. 20, 2014 is expressly incorporated by reference herein.

What is claimed is:

1. An ultrasonic device unit comprising:
    a substrate having a planar part and a recess part recessed from the planar part,
    an ultrasonic device which has an element array including a plurality of thin film ultrasonic transducer elements disposed in an array and is disposed in the recess part,
    a first flexible printed board, one end of which is superimposed on a portion of an array surface of the ultrasonic device and connected to the same, the other end of which is superimposed on a portion of the planar part and connected to the same,
    wherein the array surface of the ultrasonic device which the one end of the first flexible printed board is superimposed on is positioned within a plane including the planar part or a plane outside of the recess part.

2. The ultrasonic device unit according to claim 1, wherein a terminal connected to a terminal on the first flexible printed board is disposed in the planar part of the substrate, wherein the recess part has two mutually intersecting perpendicular surfaces at its lateral surfaces, and wherein the ultrasonic device abuts against the lateral surfaces.

3. The ultrasonic device unit according to claim 1, wherein the array surface of the ultrasonic device which the one end of the first flexible printed board is superimposed on is positioned within a plane including the planar part.

4. The ultrasonic device unit according to claim 1 further comprising a second flexible printed board, one end of which is superimposed on a portion of the array surface of the ultrasonic device and connected to the same, the other end of which is superimposed on a portion of the planar part and connected to the same, wherein a first direction is directed towards the other end from the one end of the first flexible printed board, and wherein a second direction is opposite to the first direction and directed towards the other end from the one end of the second flexible printed board.

5. The ultrasonic device unit according to claim 4, wherein the array surface of the ultrasonic device which the one end of the first flexible printed board and the one end of the second flexible printed board are superimposed on is positioned within a plane including the planar part.

6. The ultrasonic device unit according to claim 1, wherein the ultrasonic device comprises:
    a device substrate which defines opening parts individually for the thin film ultrasonic transducer elements and is provided at a first surface thereof with a vibration film closing the opening parts, and
    a plate member which is attached to a second surface of the device substrate opposite to the first surface of the device substrate, the plate member defining a ventilation path which is connected to interior spaces of the opening parts and opens at a surface facing a bottom surface of the recess part, and
    wherein a through-hole is formed in the bottom surface of the recess part so as to run through the substrate.

7. The ultrasonic device unit according to claim 1, wherein the ultrasonic device comprises:
    a device substrate which defines opening parts individually for the thin film ultrasonic transducer elements and is provided at a first surface thereof with a vibration film closing the opening parts, and
    a plate member which is attached to a second surface of the device substrate opposite to the first surface of the device substrate, the plate member defining a ventilation path which is connected to interior spaces of the opening parts and opens at a surface facing a bottom surface of the recess part, and
    wherein a void space is formed between the lateral surface of the recess part and the ultrasonic device.

8. The ultrasonic device unit according to claim 1, wherein the ultrasonic device comprises:
    a device substrate which defines opening parts individually for the thin film ultrasonic transducer elements and is provided at a first surface thereof with a vibration film closing the opening parts, and
    a plate member which is attached to a second surface of the device substrate opposite to the first surface of the device substrate, has such an area as to accommodate at least a contour of the element array in a plan view viewed from the thickness direction of the device substrate, and has a through-opening continuing from the opening part.

9. The ultrasonic device unit according to claim 8, wherein the recess part is provided at the bottom surface thereof with a through-hole which is connected to the through-opening and runs through the substrate.

10. The ultrasonic device unit according to claim 8, wherein a ventilation path is formed between the bottom surface of the recess part and the device substrate so as to be connected to the through-opening and communicate with a void space formed between the lateral surface of the recess part and the ultrasonic device.

11. A probe comprising the ultrasonic device unit according to claim 1 and a housing supporting the ultrasonic device unit.

12. An electronic device comprising the ultrasonic device unit according to claim 1 and a processing unit which is connected to the ultrasonic device unit and processes an output of the ultrasonic device unit.

13. An ultrasonic imaging device comprising the ultrasonic device unit according to claim 1, a processing unit which is connected to the ultrasonic device unit and processes an output of the ultrasonic device unit so as to create an image, and a display device for displaying the image.

* * * * *